(12) United States Patent
Kurkowski et al.

(10) Patent No.: US 6,890,757 B2
(45) Date of Patent: May 10, 2005

(54) PORTABLE DIAGNOSTIC SYSTEM

(75) Inventors: James Donald Kurkowski, Roseville, MN (US); Brian Keith Sorenson, New Brighton, MN (US); Jon Michael Tonsager, Bay City, WI (US)

(73) Assignee: International Technidyne Corporation, Roseville, MN (US)

( * ) Notice: Subject to any disclaimer, the term of this patent is extended or adjusted under 35 U.S.C. 154(b) by 241 days.

(21) Appl. No.: 10/155,519

(22) Filed: May 24, 2002

(65) Prior Publication Data

US 2003/0220583 A1 Nov. 27, 2003

(51) Int. Cl.[7] .............................................. G01N 33/49
(52) U.S. Cl. ........................ 436/68; 422/50; 422/68.1; 422/82.01; 422/82.02; 422/99; 436/150; 436/151; 436/163
(58) Field of Search ...................... 422/50, 68.1, 82.01, 422/82.02, 99, 104; 436/68, 150, 151, 163

(56) References Cited

U.S. PATENT DOCUMENTS

| | | |
|---|---|---|
| 4,225,410 A | 9/1980 | Pace |
| 4,271,119 A | 6/1981 | Columbus |
| 4,361,540 A | 11/1982 | Weinberg et al. |
| 4,397,725 A | 8/1983 | Enzer et al. |
| 4,453,151 A | 6/1984 | Leary et al. |
| 4,654,127 A | 3/1987 | Baker et al. |
| 4,654,624 A | 3/1987 | Hagan et al. |
| 4,762,594 A | 8/1988 | Guruswamy |
| 4,786,394 A | 11/1988 | Enzer et al. |
| 4,831,258 A | 5/1989 | Paulk et al. |
| 4,929,426 A | 5/1990 | Hodai et al. |
| 4,988,211 A | 1/1991 | Barnes et al. |
| 5,232,667 A | 8/1993 | Hieb et al. |
| 5,781,024 A * | 7/1998 | Blomberg et al. .......... 324/763 |

FOREIGN PATENT DOCUMENTS

| | | |
|---|---|---|
| JP | 60-128346 | 7/1985 |
| JP | 61-501873 | 8/1986 |
| JP | 1-199218 | 8/1989 |
| JP | 2-287144 | 11/1990 |
| WO | 8800708 | 1/1988 |

OTHER PUBLICATIONS http://www.seltrol.com/Exergen–IRt–c.html (Jun. 21, 2004).*
"Attention OEM's Introducing the new micro IRt/c" Exergen Corporation, date unknown.*
"SmartIRt/c Infrared Temperature Sensor" Exergen Corporation, date unknown.*

* cited by examiner

Primary Examiner—Jan M. Ludlow
(74) Attorney, Agent, or Firm—Fish & Richardson, PC PA (57) ABSTRACT

A portable system for analysis of blood or other bodily fluids removable from a patient is disclosed. The system includes a temperature sensing device and a temperature control circuit. The temperature sensing device senses a temperature of a surface of a sensor substrate of a cartridge having an electrical heater device without direct contact with the cartridge or direct exposure to the heating device. The temperature sensing device also generates an electrical signal related to the sensed temperature. The temperature control circuit controls an electrical input to the heater device based on the sensed temperature and a designed control temperature.

34 Claims, 7 Drawing Sheets

PORTABLE DIAGNOSTIC SYSTEM

FIELD

A portable diagnostic system is generally related to portable diagnostic systems based on electrochemical determinations in biological samples, and is more particularly related to a portable diagnostic system that can be connected to a larger diagnostic system having improved operating characteristics.

BACKGROUND

Methods and devices utilized for determining concentrations of electroactive species in solutions using electrochemical or electrolytic methods are well known. These instruments typically include a pair of electrochemical half cells, one of which is used as the sensor or sample half cell and the other as a reference electrode or a reference half cell. As is the case with any concentration determination of dissolved gaseous species in a liquid, the temperature at which the electrochemical determination is made needs to be known. Traditionally, blood gas determinations, for example, have been made utilizing permanently installed laboratory instrumentation to which samples are brought for analysis. Of course, in such instruments the temperature at which the sample is analyzed can be readily controlled, for example, by a constant temperature oven. These types of methods have disadvantages for portable devices. One such disadvantage is that portable devices cannot contain constant temperature ovens. Known temperature control systems for portable devices also have disadvantages. One such disadvantage is that they typically have limited operating temperature ranges. Another disadvantage is that such systems are susceptible to outside interferences. Therefore, improvements are desirable.

SUMMARY

In accordance with the present disclosure, the above and other problems are solved by the following:

In one aspect of the present disclosure, a portable system for analysis of blood or other bodily fluids removable from a patient is disclosed. The system includes a temperature sensing device and a temperature control circuit. The temperature sensing device senses a temperature of a surface of a sensor substrate of a cartridge having an electrical heater device without direct contact with the cartridge or direct exposure to the heating device. The temperature sensing device also generates an electrical signal related to the sensed temperature. The temperature control circuit controls an electrical input to the heater device based on the sensed temperature and a designed control temperature. The temperature control circuit includes capacitors arranged and configured to dampen radio frequency interference and electro static discharge.

In another aspect of the present disclosure, a portable system for analysis of blood or other bodily fluids removable from a patient is disclosed. The system includes a temperature sensing device and a temperature control circuit. The temperature sensing device senses a temperature of a surface of a sensor substrate of a cartridge having an electrical heater device without direct contact with the cartridge or direct exposure to the heating device. The temperature sensing device also generates an electrical signal related to the sensed temperature. The temperature control circuit controls an electrical input to the heater device based on the sensed temperature and a designed control temperature. The temperature control circuit is calibrated to operate at an ambient temperature at least below 14 degree Celsius.

In another aspect of the present disclosure, a portable system for analysis of blood or other bodily fluids removable from a patient is disclosed. The system includes a temperature sensing device and a temperature control circuit. The temperature sensing device senses a temperature of a surface having an analytical cell of a sensor substrate of a cartridge having an electrical heater device without direct contact with the cartridge or direct exposure to the heating device. The temperature sensing device also generates an electrical signal related to the sensed temperature. The temperature control circuit controls an electrical input to the heater device based on the sensed temperature and a designed control temperature.

In another aspect of the present disclosure, a portable system for analysis of blood or other bodily fluids removable from a patient is disclosed. The system includes a temperature sensing device and a temperature control circuit. The temperature sensing device senses a temperature of a surface, in fluid communication with an analytical cell, of a sensor substrate of a cartridge having an electrical heater device without direct contact with the cartridge or direct exposure to the heating device. The temperature sensing device also generates an electrical signal related to the sensed temperature. The temperature control circuit controls an electrical input to the heater device based on the sensed temperature and a designed control temperature.

In another aspect of the present disclosure, a method of analyzing blood or other bodily fluids removable from a patient is disclosed. The method includes inserting a cartridge, including a sensor substrate carrying an integral heater device, into a portable system and receiving results of the analysis. The portable system includes characteristics similar to those described above.

A more complete appreciation of the present invention and its scope may be obtained from the accompanying drawings, which are briefly described below, from the following detailed descriptions of presently preferred embodiments of the invention and from the appended claims.

BRIEF DESCRIPTION OF THE DRAWINGS

Referring now to the drawings in which like reference numbers represent corresponding parts throughout.

DETAILED DESCRIPTION

In the following disclosure, reference is made to the accompanying drawings that form a part hereof, and in which is shown by way of illustration specific embodiments in which the invention may be practiced. It is understood that other embodiments may be utilized and changes be made without departing from the scope of the present invention.

In general, the present disclosure describes a portable instrument that makes analytical determinations such as blood gas analysis. The instrument operates over a broader temperature range than prior known instruments and uses capacitors to dampen or reduce induced radio frequency (RF) interference and to dampen or reduce electro static discharge (ESD) susceptibility. The instrument can also be connected to a larger, more comprehensive system, such as Philips CMS and V24/V26 monitors.

In particular, the instrument uses a removable cartridge that contains a calibrated electrochemical cell designed to receive and electrochemically measure a sample injected into a sample port associated with the cartridge. The integral electrochemical cell of the cartridge is carried on a sensor chip and includes a resistive heating element also preferably formed on the sensor chip member. Electric input to the heating element is thermostatically controlled by a non-contact temperature sensitive device, such as a scanning infrared probe, that monitors the temperature of the outer surface of the sensor chip and controls input to the resistive heating element through conventional temperature control circuitry. Of course, the particular embodiment shown is merely illustrative of the several unique features and principles that may be more broadly applied by those skilled in the art.

Figure 1:
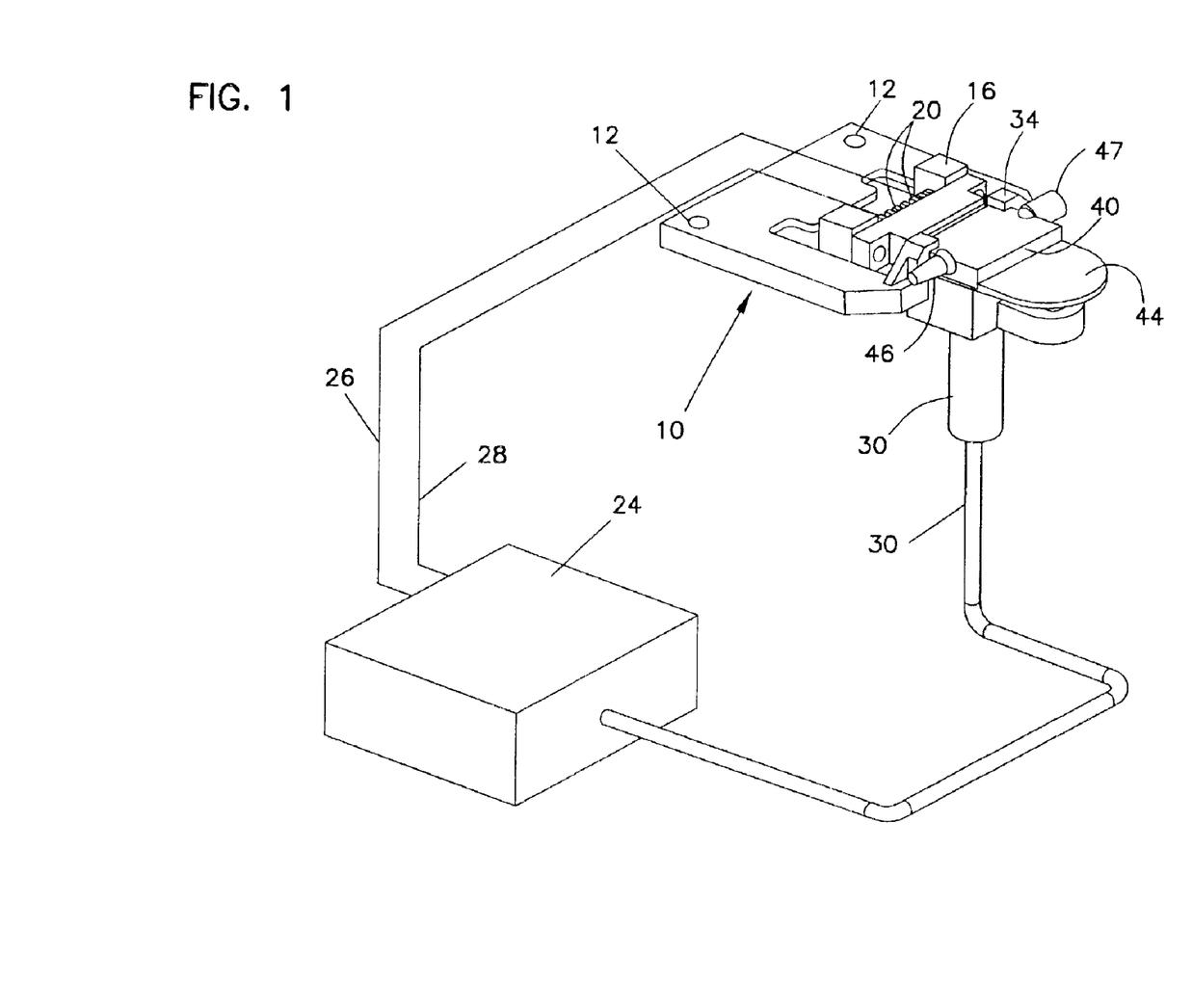
FIG. 1 is a fragmentary perspective instrument sub-assembly view.
Figure 2:
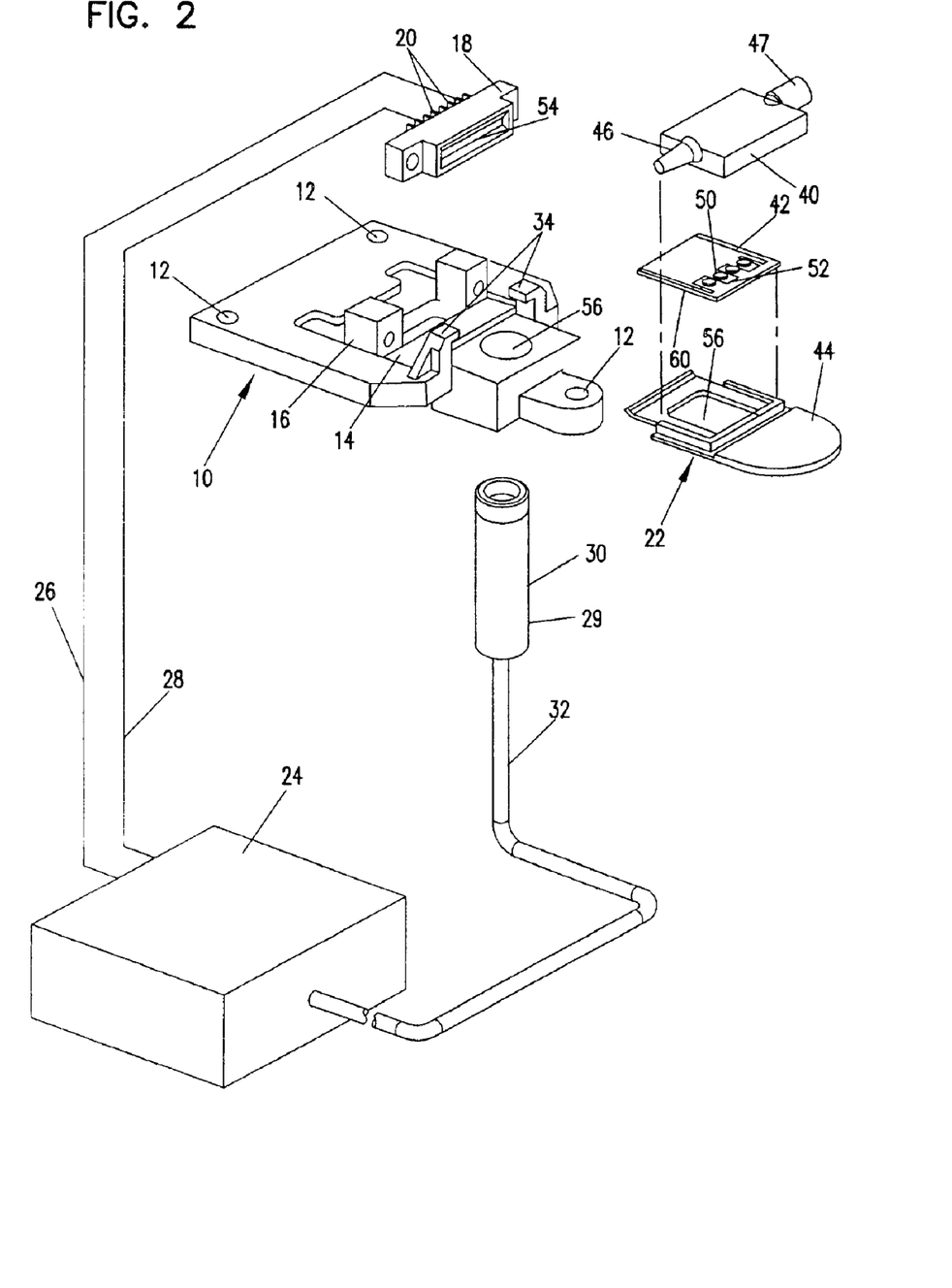
FIG. 2 is an exploded view of the sub-assembly of FIG. 1.

Referring now to FIGS. 1 and 2, an instrument sub-assembly is integral with a larger device and housing and includes a removable cartridge and cartridge receiving retaining device together with a temperature control system for the removable cartridge. The system includes an instrument sub-assembly housing, shown generally at 10, that may be fastened to the main body of a larger portable instrument (not shown) by utilizing openings or holes 12 in the housing. Referring now to FIG. 2, the housing 10 further contains a recess 14 and a connecting block 16 for receiving and retaining, as by screws (not shown), an electrical connector or terminal block 18. The connector 18 includes a plurality of electrical input/output terminals 20 that physically retain and electrically connect a removable cartridge system, depicted generally at 22, with the main portion of the analytical instrument (not shown) as required.

The connector element 18 is shown schematically connected to conventional temperature control circuitry, that operates in a well-known manner and is designated by the box 24, using a pair of conductors 26 and 28. The temperature sensing input for the temperature control system is provided by a non-contact temperature sensor 29. Preferably the temperature sensor 29 is an infrared scanning thermocouple device or probe 30 that senses temperature rapidly and accurately. The temperature probe 30 is connected to the temperature control circuitry 24 by a conduit 32. The signal received from the temperature probe 30 is processed by the temperature control circuitry 24 and compared with a value corresponding to a fixed designated set point control temperature determined by the application involved, typically about 37 degrees Celsius, which is equivalent to body temperature.

Figure 3:
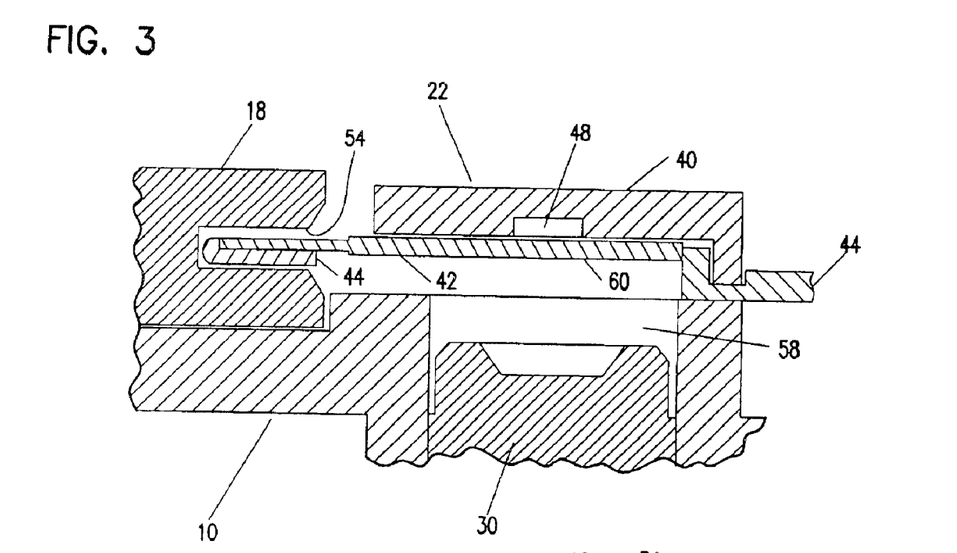
FIG. 3 is an enlarged, sectional view of a portion at the system of FIG. 1.
Figure 4:
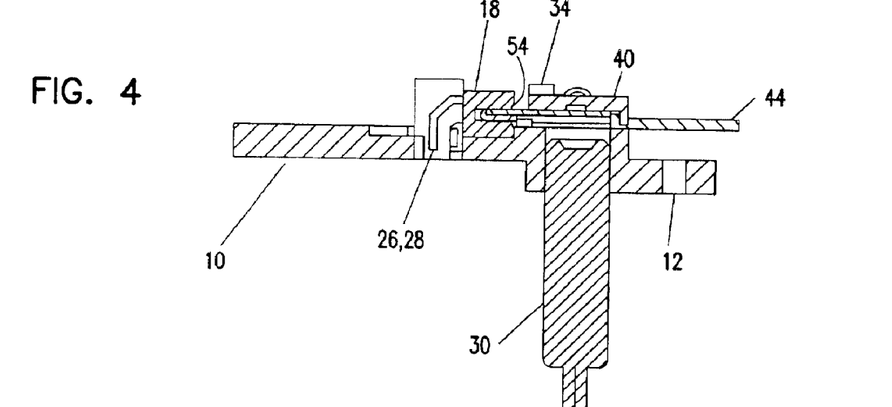
FIG. 4 is a sectional view taken substantially along line 4—4 of FIG. 5.
Figure 5:
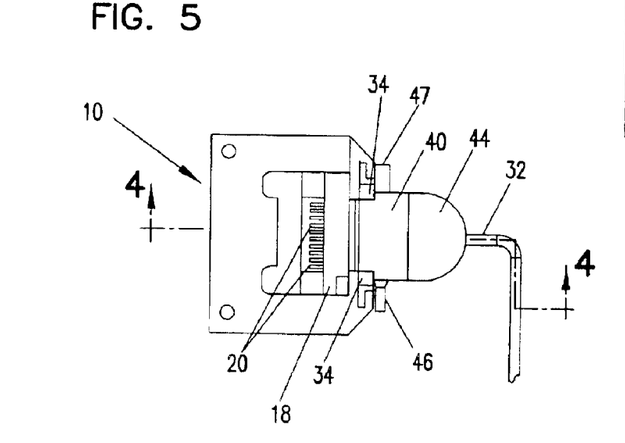
FIG. 5 is a top view of the system of FIG. 1.

The housing 10 contains a pair of integral retainers 34 that are configured to fit over and slidably receive the removable cartridge system 22. The sample cartridge 22 is depicted in exploded view in FIG. 2, and includes a top member 40, sensor chip 42 and a base member 44. The top member 40 further includes a port 46 that is used to admit a temperature probe (not shown) for experimental verification purposes. A sample receiving port is located at 47. As illustrated in FIGS. 3–5, the top member 40 contains a recess that, with the sensor chip member 42, defines a volume 48 for containing the sample. The chip 42, further contains a plurality of electrodes 50 and carries a serpentine resistance-heating element 52 that is electrically connected to the conductors 26 and 28 utilizing the connector 18 that the cartridge 22 is plugged into the recess 54. The lower member or base member 44 is recessed to receive the chip 42. The opening 56 aligns with an opening 58 provided through the housing member 10, giving the probe 30 a direct line of sight to the outer surface 60 of the chip member 42 for the purpose of temperature detection.

The probe 30 might be any suitable scanning infrared sensor, or the like. Examples include one known as IR t/c® available from Exergen Corporation of Newton, Mass. Such probes can be produced and pre-calibrated in quantity prior to manufacture of the portable measuring instruments so that they will repeatably, rapidly, and accurately control the temperature of the observed surface 60, for example, at 37 degrees Celsius±0.2 degrees Celsius. The signal produced by the temperature sensed by the probe 30 is transmitted by the conduit 32 to the control circuitry 24 that, in turn, controls the electric power in conductors 26 and 28 to modulate the energy output of the serpentine resistance element 52 in a well-known manner.

In operation, a fresh disposable cartridge 22 is inserted into the portable instrument 10 so that proper electrical connection is made in opening 54 and the cartridge 22 is also retained in place by ears 34. In connection with this operation, the temperature control system can be automatically activated by the insertion of the cartridge into the receptacle 54. The system might contain any desired time delay circuits or other activation system. Of course, the device might also be controlled by other means such as an instrument switch (not shown) in a well-known manner.

Figure 6:
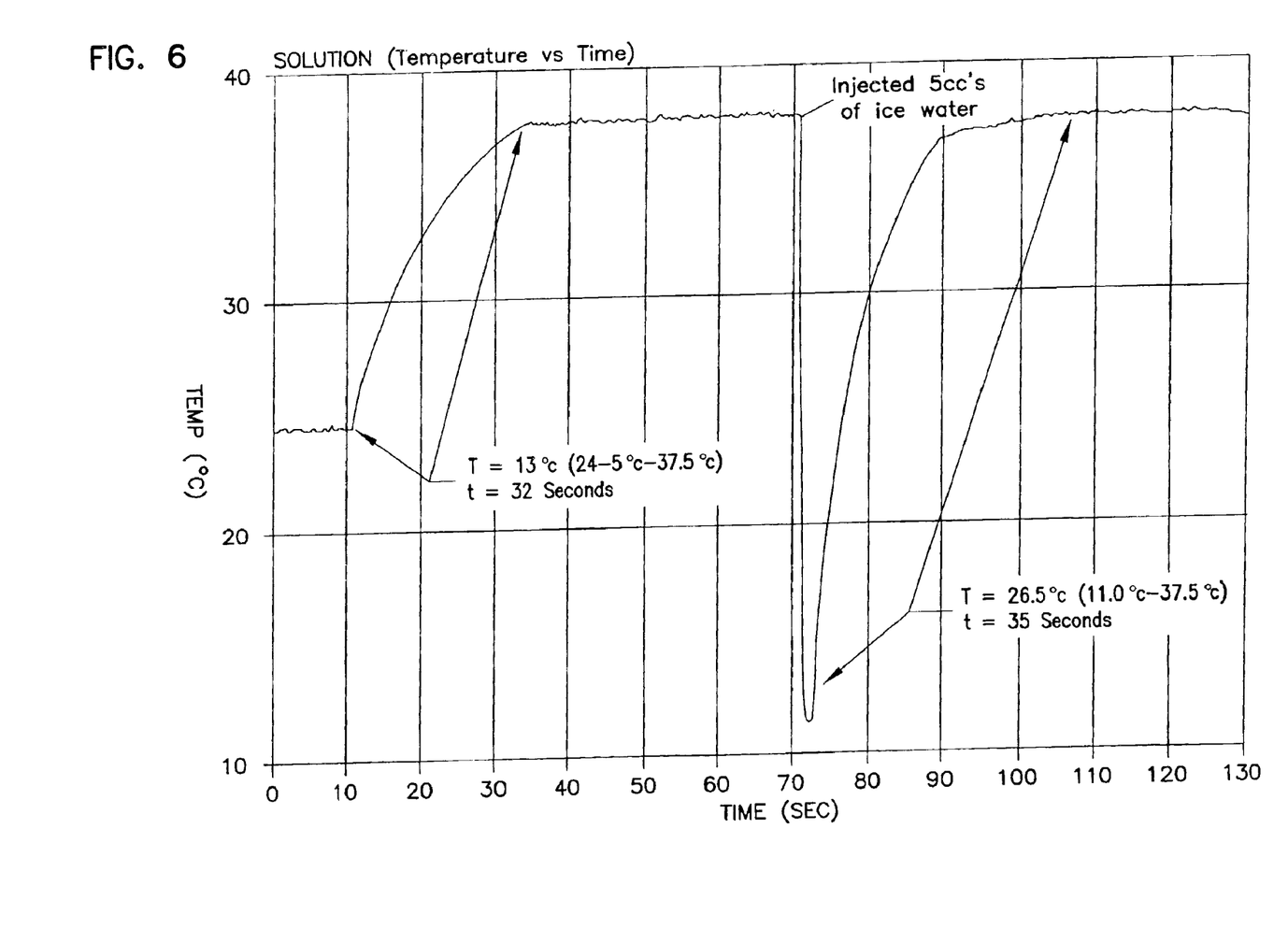
FIG. 6 is a plot depicting the temperature control of a sample solution in an electrochemical cell of a cartridge.

FIG. 6 depicts a computer generated graphical plot illustrating the ability of the temperature control system of the instrument to control the solution temperature of an analytical cell configured for selective conduction of analytical analysis, or the electrochemical cell volume 48, of a disposable cartridge 22 made in accordance with the preferred embodiment. The probe 30 and temperature control circuitry 24 are designed to control the temperature of the solution in the electrochemical cell 48 at about 37.5 degrees Celsius when stabilized. It is noted that the electrochemical cell does not need to be on the substrate but can be located elsewhere. In such a configuration, the electrochemical cell would be in fluid communications with the substrate.

The time-temperature plot of FIG. 6 illustrates the reaction of the system after activation at approximately 10 seconds into the time plot along the abscissa. The temperature data for the plot of FIG. 6 was obtained by means of a temperature probe inserted into the cell through port 46. Actual temperature values sensed by the probe may be mathematically compensated in temperatures in the cell. The time-temperature profile using the inserted temperature probe in any event is quite similar and representative of the control capabilities of the system.

As can be seen from FIG. 6, the temperature was raised from an ambient temperature of approximately 24 degrees Celsius to the control temperature of approximately 37.5 degrees Celsius at the 32-second mark. At approximately the 71-second mark, the system was shocked by the injection of approximately 5 cc of ice water as through the port 47. Within about 1–2 seconds the temperature dropped to approximately 11 degrees Celsius, the low point of the cycle. Thereafter, the recovery was again extremely rapid and reached the control point of approximately 37.5 Celsius in about 35 seconds. FIG. 6 aptly illustrates the rapidity with which the system recovers to the desired control temperature and the accuracy with which that temperature can be maintained in accordance with the invention.

The chip member 42 is normally fabricated of a ceramic with a fairly low thermal capacity for easy temperature control and quick recovery. The serpentine resistive heating element together with connecting conductors is normally deposited on the surface of the chip 42 using screen printing film or one of many well-known metalizing techniques. Such resistive heaters may be made of any conventional materials such as permalloy (an alloy having a preferred composition of 80% nickel and 20% iron). The material may be deposited as a thick or thin film in any desired configuration. The chip 42 itself may be any ceramic or other convenient dielectric material that meets the criteria for both the electrochemical cell and lends itself to temperature control utilizing the heating system of the invention.

Figure 7:
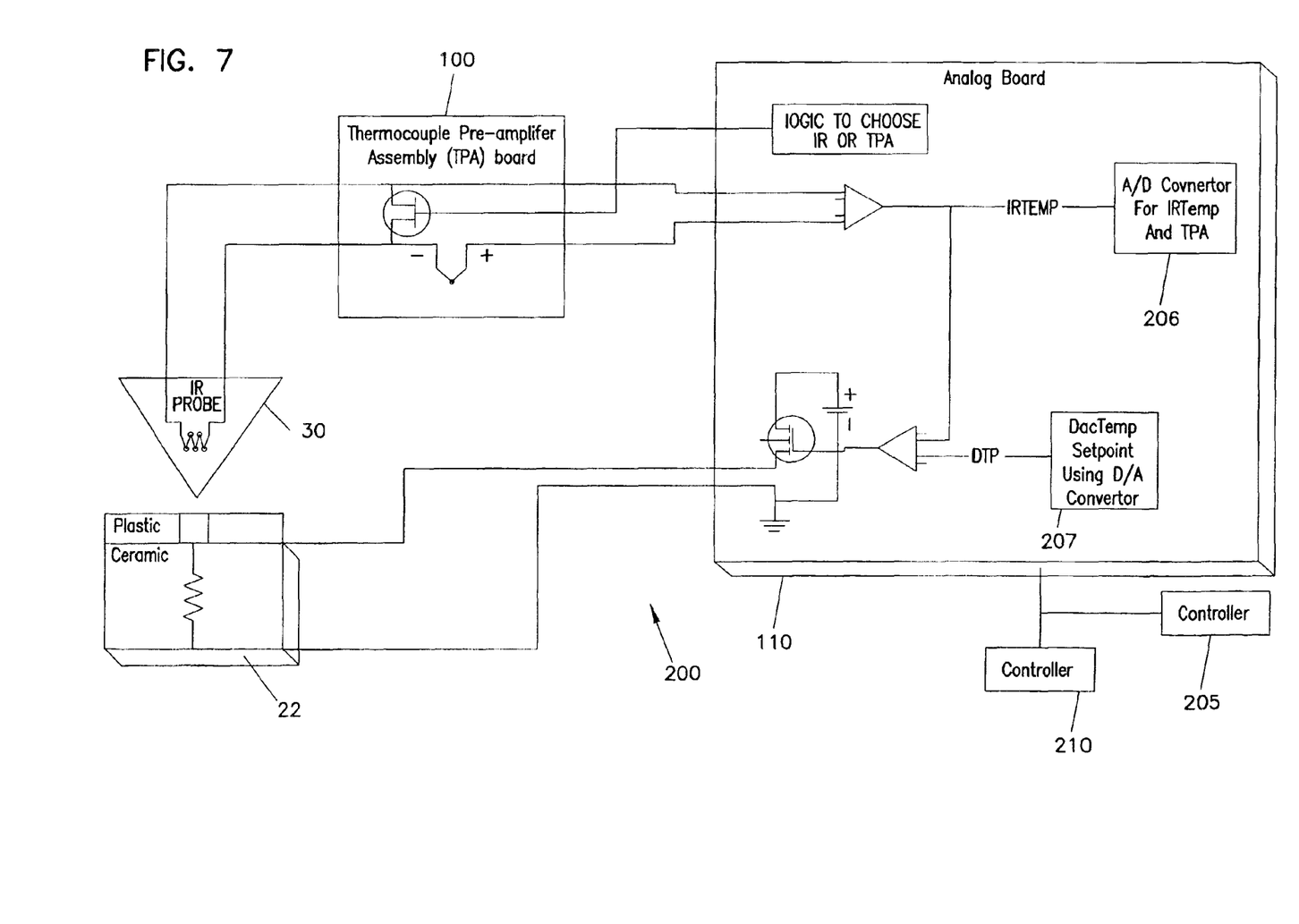
FIG. 7 is a block diagram illustrating the electrical system of the system of FIG. 1.
Figure 8:
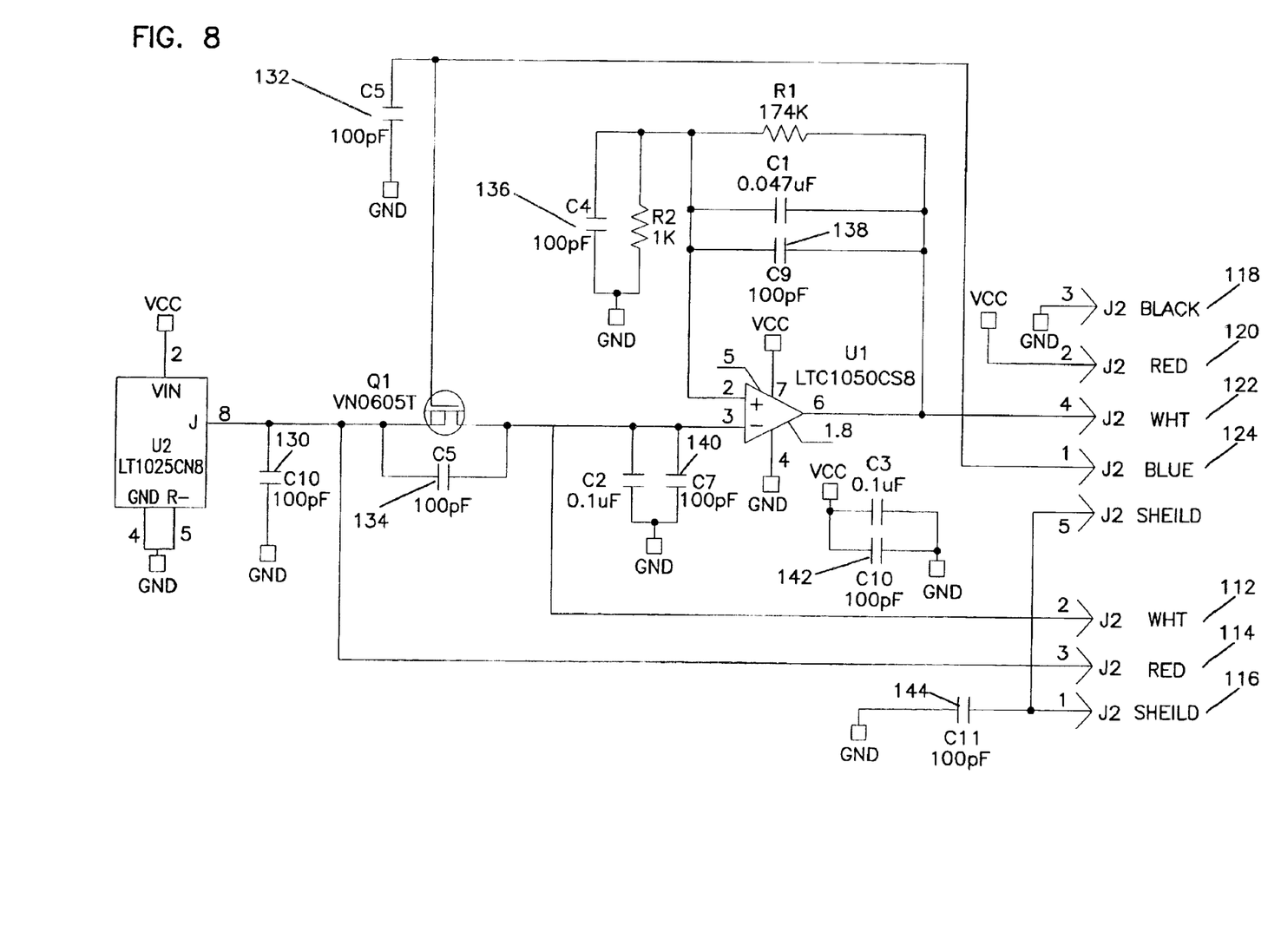
FIG. 8 is an electrical schematic of a portion of the electrical system of FIG. 7.
Figure 9:
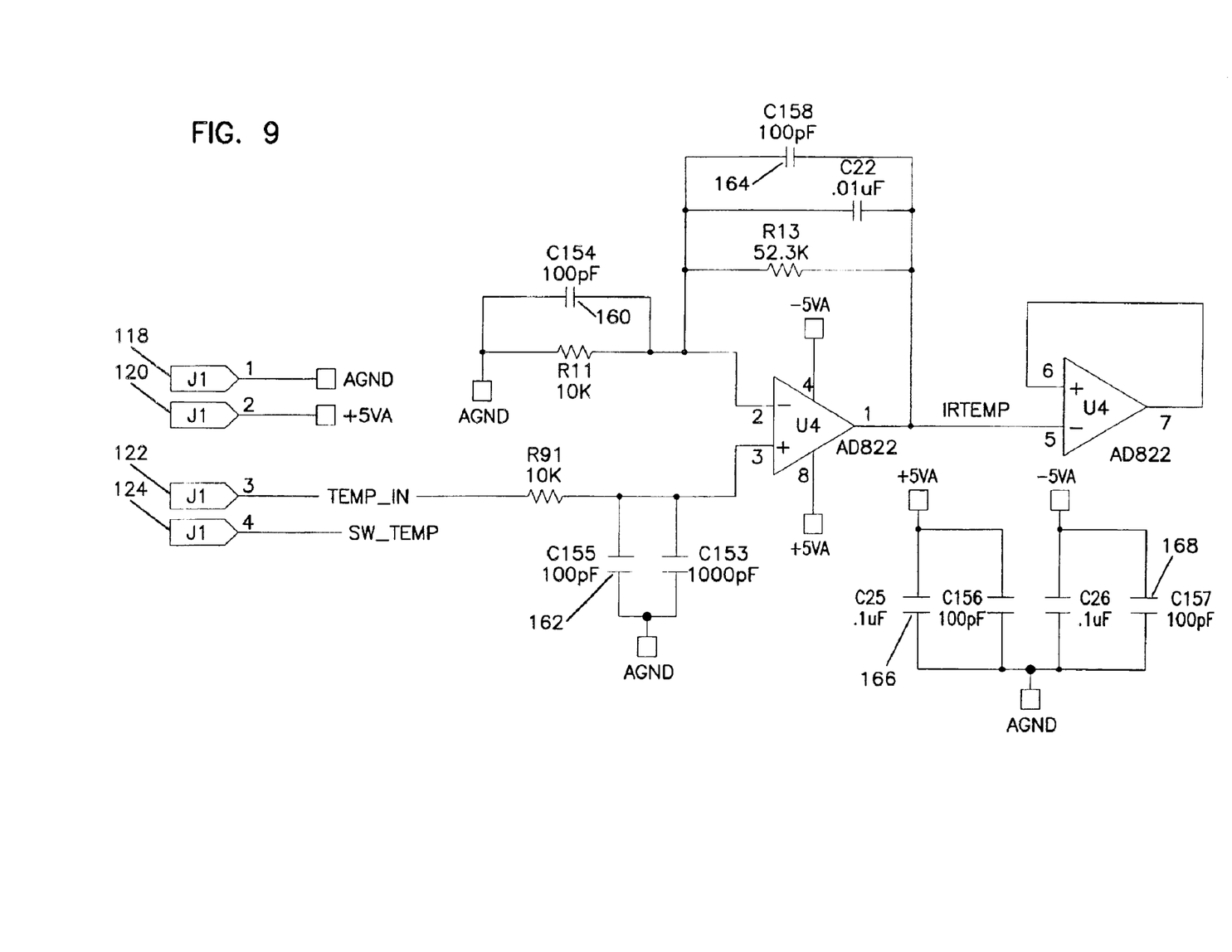
FIG. 9 is an electrical schematic of another portion of the electrical system of FIG. 7.

Attention is directed to FIGS. 7–9. FIG. 7 is a block diagram illustrating in more detail the probe 30, the cartridge system 22, and the control circuitry 24. The control circuitry 24 includes a thermocouple pre-amplifier assembly (TPA) board 100 and an analog board 110. FIG. 8 is an electrical schematic of the TPA board 100, and FIG. 9 is an electrical schematic of the analog board 110. Referring to FIG. 7, the overall system 200 includes a controller 205, or central processing unit. The controller 205 controls a A/D converter 206 and a DacTemp 207. The controller 205 also controls a port 210. The port 210 can be used to connect to a larger, more comprehensive system, such as Philips CMS and V24/V26 monitors.

Referring now to FIG. 8, the TPA board 100 is typically connected to the probe 30 by first, second, and third electrical connections 112, 114, 116. The TPA board 100 is also typically connected to the Analog board 110 by fourth, fifth, sixth, and seventh electrical connections 118, 120, 122, 124. The TPA board 100 includes decoupling capacitors 130, 132, 134, 136, 138, 140, 142, 144. These decoupling capacitors 130, 132, 134, 136, 138, 140, 142, 144 are arranged and configured to absorb energy to dampen or reduce induced RF interference and ESD. These decoupling capacitors 130, 132, 134, 136, 138, 140, 142, 144 are advantageous because they improve overall performance of the control circuitry 24 and enable operation in a wider variety of conditions. On example is that the capacitors 132, 134, 136, 138, 140, 142, 144 eliminate the need for shielding in the shell or case of the instrument.

Referring now to FIG. 9, likewise, the analog board 110 includes decoupling capacitors 160, 162, 164, 166, 168. These decoupling capacitors 160, 162, 164, 166, 168 are arranged and configured to absorb energy to dampen or reduce induced RF interference and ESD, eliminating the need for shielding in the shell or case of the instrument. One skilled in the art will recognize that the number, placement, and capacitance of the decoupling capacitors could be varied to achieve similar results or improved energy absorption.

Referring back to FIG. 7, the overall system 200 is calibrated prior to use. Data is gathered over the range of the operating temperature to establish constants to be employed during a test of a cartridge 22. The constants are used to control the system 200 to between 36 degrees Celsius and 38 degrees Celsius, the typical temperature of the cartridge 22 during testing. The system 200 can be calibrated for an external, or ambient, operating temperature range of 12 degrees Celsius to 30 degrees Celsius, or a temperature range of at least below 14 degrees Celsius inclusive. This temperature range is advantageous because the system can be used in a larger variety of external environments having different temperature conditions.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present disclosure which is set forth in the following claims.

What is claimed is:

1. A portable system for analysis of blood or other bodily fluids removable from a patient, the portable system comprising:
   a temperature sensing device for sensing a temperature of a surface of a sensor substrate of a cartridge having an electrical heater device without direct contact with the cartridge and without direct exposure to the heating device and generating an electrical signal related to the sensed temperature; and
   a temperature control circuit for controlling an electrical input to the heater device based on the sensed temperature and a designed control temperature, and the temperature control circuit including capacitors arranged and configured to dampen radio frequency interference and electro static discharge.

2. The system of claim 1, wherein the temperature control circuit is calibrated to operate at an ambient temperature at least below 14 degrees Celsius.

3. The system of claim 1, wherein the temperature sensing device is an infrared probe.

4. The system of claim 1, wherein the electrical heater device is a resistance heater integral with one surface of the sensor substrate.

5. The system of claim 4, wherein the electrical heater device is a film resistor and the sensor substrate is a dielectric chip.

6. The system of claim 1, wherein the surface of which the temperature is sensed is a sensor substrate surface opposite that carrying an analytical cell configured for selective conduction of analytical analysis of the blood and other body fluids.

7. The system of claim 1, wherein the surface of which the temperature is sensed is a sensor substrate surface that carries an analytical cell.

8. The system of claim 1, further including a port for communication with an external system.

9. The system of claim 1, further including the cartridge operably mounted in the device.

10. A portable system for analysis of blood or other bodily fluid removable from a patient, the portable system, comprising:
    a temperature sensing device for sensing a temperature of a surface of a sensor substrate of a cartridge having an electrical heater device without direct contact with the cartridge and without direct exposure to the heating device and generating an electrical signal related to the sensed temperature;
    a temperature control circuit for controlling an electrical input to the heater device based on the sensed temperature and a designed control temperature, and the temperature control circuit being calibrated to operate at an ambient temperature at least below 14 degrees Celsius; and wherein the temperature control circuit includes capacitors arranged and configured to dampen radio frequency interference and electro static discharge.

11. The system of claim 10, wherein the temperature sensing device is an infrared probe.

12. The system of claim 10, wherein the electrical heater device is a resistance heater integral with one surface of the sensor substrate.

13. The system of claim 12, wherein the electrical heater device is a film resistor and the sensor substrate is a dielectric chip.

14. The system of claim 10, wherein the surface of which the temperature is sensed is a sensor substrate surface opposite that carrying an analytical cell configured for selective conduction of analytical analysis of the blood and other body fluids.

15. The system of claim 10, wherein the surface of which the temperature is sensed is a sensor substrate surface that carries the electrochemical cell means.

16. The system of claim 10, further including a port for communication with an external system.

17. The system of claim 10, further including the cartridge operably mounted in the device.

18. A portable system for analysis of blood or bodily fluids removable from a patient, the portable system, comprising:

a temperature sensing device for sensing a temperature of a surface having an analytical cell of a sensor substrate of a cartridge having an electrical heater device without direct contact with the cartridge and without direct exposure to the heating element and generating an electrical signal related to the sensed temperature;

a temperature control circuit for controlling an electrical input to the heater device based on the sensed temperature and a designed control temperature; and wherein the temperature control circuit includes capacitors arranged and configured to dampen radio frequency interference and electro static discharge.

19. The system of claim 18, wherein the temperature control circuit being calibrated to operate at an ambient temperature at least below 14 degrees Celsius.

20. The system of claim 18, wherein the temperature sensing device is an infrared probe.

21. The system of claim 18, wherein the electrical heater device is a resistance heater integral with one surface of the sensor substrate.

22. The system of claim 21, wherein the electrical heater device is a film resistor and the sensor substrate is a dielectric chip.

23. The system of claim 18, further including the cartridge operably mounted in the device.

24. A portable system for analysis of blood or other bodily fluids removable from a patient, the portable system comprising:

a temperature sensing device for sensing a temperature of a surface, in fluid communication with an analytical cell, of a sensor substrate of a cartridge having an electrical heater device without direct contact with the cartridge and without direct exposure to the heating device and generating an electrical signal related to the sensed temperature;

a temperature control circuit for controlling an electrical input to the heater device based on the sensed temperature and a designed control temperature; and wherein the temperature control circuit includes capacitors arranged and configured to dampen radio frequency interference and electro static discharge.

25. The system of claim 24, wherein the temperature control circuit is calibrated to operate at an ambient temperature at least below 14 degrees Celsius.

26. The system of claim 24, wherein the temperature sensing device is an infrared probe.

27. The system of claim 24, wherein the electrical heater device is a resistance heater integral with one surface of the sensor substrate.

28. The system of claim 27, wherein the electrical heater device is a film resistor and the sensor substrate is a dielectric chip.

29. The system of claim 24, further including a port for communication with an external system.

30. The system of claim 24, further including the cartridge operably mounted in the device.

31. A method of analyzing blood or other bodily fluids removable from a patient, the method comprising:

inserting a cartridge, including a sensor substrate carrying an integral heater device, into a portable system including capacitors arranged and configured to dampen radio frequency interference and electro static discharge;

sensing a temperature of a surface of the sensor substrate without direct contact with a cartridge or direct exposure to the heating device;

generating an electrical signal related to the sensed temperature;

controlling an electrical input to the heater device based on the sensed temperature and a designed control temperature; and displaying results of the analysis.

32. A method according to claim 31, further including connecting a port of the portable system to an external system.

33. A method according to claim 31, wherein inserting a cartridge into a portable system includes inserting a cartridge into a portable system wherein the surface includes an analytical cell.

34. A method according to claim 31, wherein inserting a cartridge into a portable system includes inserting a cartridge into a portable system wherein the surface is in fluid communication with an analytical cell.

* * * * *

UNITED STATES PATENT AND TRADEMARK OFFICE
CERTIFICATE OF CORRECTION

PATENT NO. : 6,890,757 B2  
APPLICATION NO. : 10/155519  
DATED : May 10, 2005  
INVENTOR(S) : James D. Kurkowski, Brian K. Sorenson and Jon M. Tonsager It is certified that error appears in the above-identified patent and that said Letters Patent is hereby corrected as shown below:

Column 7, line 22 (Claim 15), please delete "surface".

Signed and Sealed this

Twenty-fifth Day of July, 2006

JON W. DUDAS  
*Director of the United States Patent and Trademark Office*